United States Patent [19]

Halloran

[11] Patent Number: 4,985,240

[45] Date of Patent: Jan. 15, 1991

[54] ODOR-FREE PERM

[75] Inventor: Daniel J. Halloran, Midland, Mich.

[73] Assignee: Dow Corning Corporation, Midland, Mich.

[21] Appl. No.: 482,123

[22] Filed: Feb. 20, 1990

[51] Int. Cl.$^5$ .......................... A61K 7/09; A45D 7/04
[52] U.S. Cl. ..................................... 424/71; 514/772; 132/204
[58] Field of Search .................. 424/71; 132/203, 204; 514/772

[56] References Cited

U.S. PATENT DOCUMENTS 2,782,790  2/1957  Hersh et al. ............................. 132/7
2,787,274  4/1957  Gant ................................. 424/71 X

FOREIGN PATENT DOCUMENTS 746037  3/1953  United Kingdom .
746038  3/1953  United Kingdom .
751992  3/1957  United Kingdom .

*Primary Examiner*—Merrell C. Cashion, Jr.
*Assistant Examiner*—Susan S. Rucker
*Attorney, Agent, or Firm*—Sharon K. Severance

[57] ABSTRACT

Disclosed is a method of perming hair by applying to the hair a solution containing an alkali metal or alkaline earth metal siliconate. The siliconates are used in place of typical reducing agents. The perms produce no odor due to the absence of —SH functionality in the perming solutions.

3 Claims, No Drawings

ODOR-FREE PERM

This invention pertains to the use of alkali or alkaline earth metal siliconates (herein referred to only as metal siliconate) in hair straightening or curling processes which typically involve the use of reducing agents. The metal siliconates are substituted for typical reducing agents thereby eliminating the use of sulfur containing compounds and the odor associated with the sulfur containing compounds.

BACKGROUND OF THE INVENTION

The process for straightening or curling of hair (herein referred to as perming permed or perm), currenty known in the art, involves the use of sulfur based reducing agents to break the keratin disulfide (K—S—S—K) bonds in the hair. The hair is then fixed in the permed state using oxidizing agents such as hydrogen peroxide, to create new K—S—S—K bonds in the hair. A perming composition is typically comprised of both a reducing agent and an oxidizing agent which are applied independently and separately to the hair.

The sulfur containing reducing agents known in the art include thioglycolic acid, salts of thioglycolic acid and other —SH containing materials including organic polymers, silicones and polysiloxanes. These materials all have the odor that is commonly associated with thioglycolic acid due to the presence of the —SH bond in the materials. Modification of the thioglycolic acid by creating a salt or adding the —SH functionality onto a polymer backbone has shown some reduction in odor, however, the odor has not been eliminated. Masking of the odor using fragrances or other materials is also ineffective. A truly odor-free perm composition is not known in the art because current technology known in the art uses compounds which contain the —SH functionality to reduce the hair.

This invention pertains to the use of metal siliconates, which contain no —SH functionality, that are useful as the reducing agents in the perming of hair. The hair is oxidized into the new state (cur ed or straight) using oxidizing agents known in the art, such as hydrogen peroxide. Because there is no —SH functionality employed in the perming process, a truly odor-free hair perming process results.

Several organopolysiloxane compositions are known in the art for use in the perming process. For example, Great Britain Pat. No. 751,992 teaches a method for preparing water-soluble organosilicon compositions. Alkoxysilanes are hydrolyzed by heating them with water until a homogeneous solution is obtained. These water-soluble organosilicon compositions are described as being useful for preventing hair from kinking or Prolonging the life of permanent waves. These materials are not taught as being useful in the introduction of the curls or directly in the perming process.

U.S. Pat. No. 2,782,790 to Hersh et al. teaches a composition for straightening or curling hair. This composition consists of hydrolyzable organosilanes and other optional materials. Aluminum hydroxide is taught as one optional ingredient but only to act as a catalyst for gellation and not to form in-situ metal siliconates. The perms formed by the composition as taught by Hersh et al. are "in-situ" or non-reducing type perms where the organosilanes do not react directly with the hair.

It is an object of this invention to show an odor-free method of perming hair.

It is further an object of this invention whereby the odor-free method of perming hair is achieved by the use of metal siliconates as the reducing agent (K—S—S—K bond breaking agent).

THE INVENTION

This invention pertains to a method of perming hair whereby metal siliconates are used in place of the reducing agents known in the art. In this invention the hair is washed and set. A solution containing a metal siliconate is applied to the hair. After sufficient reduction of the K—S—S—K bonds in the hair has been achieved the hair is rinsed with water and an oxidizing agent is applied. Upon completion of oxidation the hair is rinsed again with water and styled in the desired manner. Because the solution containing the metal siliconate does not contain —SH containing materials an odor-free method of perming hair is achieved.

Metal siliconates useful in the instant invention can be described by the general formula:

$$R_a—Si—(O^-M^+)_{4-a}$$

where each R is independently selected from a saturated or unsaturated alkyl group containing 1 to 6 carbon atoms, an aryl group containing 6 to 10 carbons, a halogen atom, a haloalkyl group containing 1 to 6 carbons, an amino alkyl group containing 1 to 6 carbons, a phosphonoalkyl group containing 1 to 6 carbon atoms, a carboxyalkyl group containing 1 to 6 carbon atoms, and an acryloxy group of the general formula $$R^1—\overset{\overset{O}{\|}}{C}—O—R^2—$$

wherein $R^1$ is selected from an alkyl group containing 1 to 6 carbon atoms, an aryl group containing 6 to 10 carbons; and $R^2$ is selected from a saturated alkylene group containing 1 to 6 carbon atoms, and an arylene group containing 6 to 10 carbons; M is selected from an alkali metal an alkaline earth metal and ammonium compounds; and a has the value of 0 to 3.

R can be further exemplified by alkyl groups such a methyl, ethyl, propyl, and vinyl; aryl groups such as phenyl; halogens such as chlorine, bromine and fluorine, halogenalkyls such as chloromethy and chloroethyl; and acryloxy's such as $CH_3—C(O)—O—CH_2—$.

M can be further exemplified by sodium, potassium, calcium, barium, and strontium, ammonium and organic ammoniums. The preferred metals include sodium, potassium and ammonium. The metal siliconates useful in the instant invention can be exemplified by but are not limited to,

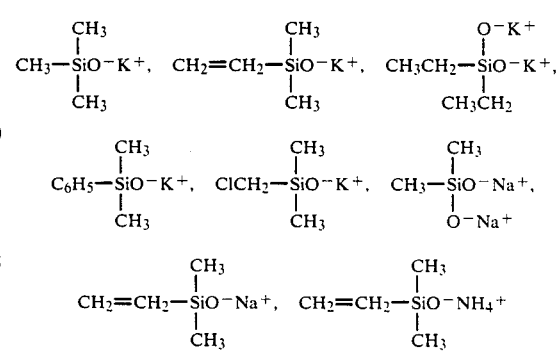

-continued

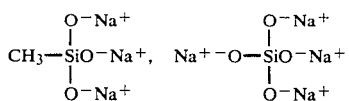

The metal siliconates useful in the instant invention are typically prepared by the reaction between a silane containing at least one hydrolyzable group and an ammonium, alkali or alkaline earth hydroxide (herein referred to only as metal hydroxide). The hydrolyzable group on the silane can include, but is not limited to, the —OH group, alkoxy groups such as methoxy (—OCH$_3$) or ethoxy (—OCH$_2$CH$_3$), the group —OR$^3$ where R$^3$ is an aryl group consisting of 6 to 10 carbon atoms, and a halogen atom. Because of the by-product formation in the reaction of producing the metal siliconate it is preferred to use silanes with a hydrolyzable groups such as -OH and alkoxy.

A method for preparing the metal siliconates comprises mixing a silane containing a hydrolyzable group with an aqueous, aqueous/alcohol or aqueous/solvent solution of a metal hydroxide. It is preferred to use about 1 mole of metal hydroxide per mole of hydrolyzable groups on the silane when the hydrolyzable group is an alkoxy group or the group -OH thereby resulting in the formation of the metal siliconate and an alcohol or water. When the hydrolyzable group is a halogen atom, or the group —OR$^3$ it is preferable to use about two moles of the metal hydroxide per mole of the hydrolyzable group on the silane thereby resulting in the formation of the metal siliconate, the metal salt of the hydrolyzable group and water.

Solutions which comprise mixtures of the hydrolyzable silane and the metal siliconate can be produced by reacting less than the necessary amount of metal hydroxide per mole of hydrolyzable group. These solutions in which the hydrolyzable silane is not fully reacted into the metal siliconate have also been found to be useful as substitutes for reducing agents in the perming of hair. A sufficient conversion of the silane which contains the hydrolyzable group into the metal siliconate should be ensured to allow for the perming of hair. It is preferred that at least 5% by weight of the hydrolyzable silane be converted into the metal siliconate. These solutions may further contain partially condensed silanes due to the presence of water.

It is not necessary to apply heat to allow for the reaction to occur between the silane and the metal hydroxide. Temperatures below the boiling points of the reactants and reaction products can be applied to ensure or aide in providing a homogenous solution.

The reaction to produce the metal siliconates can be carried out in a solvent. The solvent should be one that offers compatibility between the hydrolyzable silane and the metal hydroxide as well as the reaction products. The solvent should also show low or no reactivity with the hydrolyzable silane. Typical solvents useful for carrying out the reaction include water and alcohols such as methanol, ethanol, and iso-propanol.

The metal siliconates may be optionally recovered and dried into a powdered form, purified and resolubilized or they may be left in the solution in which they were prepared for application to the hair. Purification of the metal siliconate is not required for them to be useful in the perming of hair.

The metal siliconates can be combined with diluents for application to the hair. Typical diluents include alcohols, water, low molecular weight silicones, isoparaffins, low molecular weight alkanes and others. It is preferred that the metal siliconate comprise 0.1 to 50 percent by weight of the total diluted solution. In the process of forming the metal siliconates it is not necessary to remove the by-product prior to diluting or application to the hair. In some instances the by-product and diluent may be the same, such as when the by-product is methanol or ethanol.

The solution containing the metal siliconate may also contain optional ingredients which aide in the conditioning of the hair during the perming process or provide other aesthetic properties to the hair during or after the perming process. These materials should be unreactive with the metal siliconates in the solution. These materials may be exemplified by other silicones, vitamins, herbal extracts, buffering agents, perfumes, fragrances and others.

The method of perming the hair is one known in the art except that the traditional reducing agent is replace with a solution comprising the metal siliconate. The solution containing the metal siliconate is applied to the hair after it has been set in typical perming means, such as rods. It may be desirable, however, to apply some or all of the solution prior to setting the hair in the perming means. It is not necessary that the hair be wet prior to application of the metal siliconate solution, however, hair that has been wetted is easier to set in the perming means and the application of the metal siliconate to the hair may be aided by the wetness of the hair. Once the metal siliconate has been evenly applied to the hair or portions of hair to which curling or straightening is desired, the hair is allowed to stand for a period of time at room temperature or greater, If heat is applied during the treatment with the metal siliconate it is preferred that temperature be kept below 60° C. The period of time the hair is allowed to stand in contact with the metal siliconate solution is determined by the amount of curl or straightness desired in the hair and the ease to which the hair is reduced. Typically, 5 to 40 minutes is sufficient to provide sufficient reduction, thereby imparting curl or straightness to the hair. It may be desirable to loosely cover the hair with plastic or similar material for the period of time the metal siliconate is applied to prevent full drying of the hair during the treatment.

After the desired amount of reduction of the hair has been obtained with the metal siliconate solution, the hair is rinsed with water, blotted dry and a typical oxidizing agent is applied Aqueous hydrogen peroxide is the agent known in the art and most commonly used for oxidation of the hair. The oxidizing agent may contain additional ingredients that aide in the conditioning of the hair or provide other aesthetic properties. The oxidizing agent is evenly applied to the reduced hair and is allowed to stand in contact with the hair for a period of time. Again this period of time is determined by the degree of oxidation required to produce the curl or straightness desired. Typically 2 to 15 minutes is sufficient for complete oxidation. After the hair has been oxidized, the hair is again thoroughly rinsed with water and styled in the desired manner.

The metal siliconates can also be used in alkaline hair straightening processes which require an alkaline solution to "digest" the hair. The metal siliconates are substituted for the alkaline solutions known in the art that are used to digest the hair. Further treatment is completed with materials known in the art.

So that those skilled in the art can understand and appreciate the invention taught herein, the following examples are presented, it being understood that these examples should not be used to limit the scope of this invention over the imitations found in the claims attached hereto.

PREPARATION OF METAL SILICONATES

Example 1

1 gram of Et₃SiOH (where Et represents an ethyl group) was combined with 9 grams of ethanol. The silane was mixed with a 1.31 gram solution consisting of 0.51 grams KOH and 0.8 grams of deionized water. A homogeneous solution resulted.

Example 2

1 gram of Me₃SiOPh (where Me represents a methyl group and Ph represents a phenyl group) was combined with 9 grams of ethanol. The silane was mixed with a 1.85 gram solution consisting of 0.85 grams KOH and 1.0 grams of deionized water. A homogeneous solution resulted.

Example 3

1 gram of Me₂PrSiCl (where Me represents a methyl group and Pr represents a propyl group was combined with a 1.23 gram solution consisting of 0.53 grams KOH and 0.7 grams of deionized water. A homogeneous solution resulted.

Example 4

1 gram of Me₂PhSiOEt (where Me represents a methyl group and Ph represents a phenyl group and Et represents an ethyl group) was combined with 9 grams of ethanol. The silane was mixed with a 1.0 gram solution consisting of 0.36 grams KOH and 0.7 grams of deionized water. A homogeneous solution resulted.

Example 5

1 gram of H₂C=CHMe₂SiOEt (where Me represents a methyl group and Et represents an ethyl group) was combined with 9 grams of ethanol. The silane was mixed with a 1.24 gram solution consisting of 0.54 grams KOH and 0.7 grams of deionized water. A homogeneous solution resulted.

Example 6

1 gram of ClCHMe₂SiCl (where Me represents a methyl group was combined with 9 grams of ethanol. The silane was mixed with a 1.48 gram solution consisting of 0.78 grams KOH and 0.7 grams of deionized water. A homogeneous solution resulted.

Example 7

1 gram of Ph₃SiOH (where Ph represents a phenyl group) was combined with 9 grams of ethanol. The silane was mixed with a 0.95 gram solution consisting of 0.25 grams KOH and 0.7 grams of deionized water. A homogeneous solution resulted.

Hair Perming Tests

The above samples were tested for the ability to curl hair. A standard waving solution (ammonium thioglycolate) was run as a comparison (example A). A second comparison example p) was run using a solution consisting of 9 grams of ethanol, 0.55 grams KOH and 0.8 grams of deionized water.

The perm was conducted by combing approximately 1 gram of the perming (reducing) solution (as prepared in Examples 1 to 7) onto freshly shampooed, 2 gram, samples of hair. The hair was then rolled onto standard waving rods and another gram of the perming (reducing) solution was applied. The rods containing the hair were placed in a bag and placed in a 40° C. oven for 20 minutes. The rods containing the hair were then removed from the bag and rinsed with tap water and blotted dry. The rods were then allowed to set in a solution of 6% aqueous hydrogen peroxide for about 2 minutes. They were place in the bag again and placed in the 40° C. oven for 5 minutes. The hair was then unrolled from the rods, massaged by hand, rinsed under tap water and hung up to dry. The results of curl of wet and dry properties are in Table I.

TABLE I

| EXAMPLE | INITIAL CURL | WET COMB |
|---|---|---|
| 1 | good | good |
| 2 | good | good |
| 3 | good | good |
| 4 | good | good |
| 5 | good | good |
| 6 | slight | excellent |
| 7 | slight | good |
| A | excellent | poor |
| B | poor | horrible | n/a = not available

It is believed that those metal siliconates that produced only a slight to some curl resulted from the high PH of the metal siliconate solution. Because of the high pH incomplete neutralization (oxidation) with the hydrogen peroxide resulted. The tress from example B (KOH, ethanol and water) was very badly damaged. There was no odor associated with the metal siliconate solution or the tresses permed with the metal siliconate solution. Some conditioning was also provided to the tresses which were permed using the metal siliconate solution.

What is claimed is:

1. A method of perming hair comprising
(A) reducing the hair by applying to the hair a solution comprising a metal siliconate of the general formula

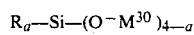

$$R_a-Si-(O^-M^{30})_{4-a}$$

wherein each R is independently selected from a saturated or unsaturated alkyl group containing 1 to 6 carbon atoms, an aryl group containing 6 to 10 carbons, a halogen atom, a haloalkyl group containing 1 to 6 carbons, and an acryloxy group of the general formula

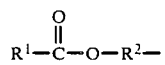

$$R^1-\overset{O}{\underset{\|}{C}}-O-R^2-$$

where R¹ is selected from an alkyl group containing 1 to 6 carbon atoms, an aryl group containing 6 to 10 carbons and is selected from a saturated alkylene group containing 1 to 6 carbon atoms, and an arylene group containing 6 to 10 carbons; M is selected from an alkali metal, an alkaline earth metal and ammonium compounds; and a has the value of 0 to 3; and (B) oxidizing the hair by applying to the hair an oxidizing agent.

2. A method as claimed in claim 1 wherein M is selected from sodium, potassium and ammonium.

3. A method as claimed in claim 2 wherein the metal siliconate is represented by the formula $$R_a-Si-(O^-K^+)_{4-a}$$

where R and a are as described above.

* * * * *

UNITED STATES PATENT AND TRADEMARK OFFICE
CERTIFICATE OF CORRECTION

PATENT NO. : 4,985,240

DATED : January 15, 1991

INVENTOR(S) : Daniel Joseph Halloran

It is certified that error appears in the above-identified patent and that said Letters Patent is hereby corrected as shown below:

In Column 1, line 15, "perming permed" should read --perming, permed--.

In Column 1, line 42, "cur ed" should read --(curled --.

In Example 3, Column 5, line 29, "propyl group was" should read -- propyl group) was --.

In Example 6, Column 5, line 52, "methyl group was" should read -- methyl group) was --.

In Column 5, line 68, "comparison example p)" should read --comparison (example B) --.

In Claim 1, Column 6, line 50, "$R_a-Si(O^- M^{30})4-a$ should read -- $R_a-Si-(O^- M^+) 4-a$ --.

In Claim 1, Column 6, line 65, "to 10 carbons and is selected" should read -- to 10 carbons and $R^2$ is selected --.

Signed and Sealed this

Nineteenth Day of May, 1992

Attest:

DOUGLAS B. COMER

*Attesting Officer*    *Acting Commissioner of Patents and Trademarks*